United States Patent [19]

Tischer

[11] Patent Number: 4,655,216

[45] Date of Patent: Apr. 7, 1987

[54] COMBINATION INSTRUMENT FOR LAPAROSCOPICAL TUBE STERILIZATION

[76] Inventor: Alfred Tischer, Potsdamer Strasse 105, 1000 Berlin 30, Fed. Rep. of Germany

[21] Appl. No.: 758,165

[22] Filed: Jul. 23, 1985

[51] Int. Cl.⁴ .............................................. A61B 17/36
[52] U.S. Cl. ................................. 128/303.17; 128/751
[58] Field of Search ........... 128/303.1, 303.13–303.17, 128/305–318, 749–754

[56] References Cited

U.S. PATENT DOCUMENTS

| | | | |
|---|---|---|---|
| 1,683,708 | 9/1928 | Wappler et al. | 128/303.16 |
| 1,881,250 | 10/1932 | Tomlinson | 128/303.16 |
| 2,004,559 | 6/1935 | Wappler et al. | 128/303.17 |
| 2,068,721 | 1/1937 | Wappler et al. | 128/303.17 |
| 3,404,677 | 10/1968 | Springer | 128/751 |
| 3,831,607 | 8/1974 | Lindemann | 128/303.17 |
| 4,005,714 | 2/1977 | Hiltebrandt | 128/303.17 |
| 4,016,881 | 4/1977 | Rioux et al. | 128/303.17 |
| 4,243,047 | 1/1981 | Olsen | 128/751 |
| 4,369,788 | 1/1983 | Gould | 128/751 |
| 4,418,692 | 12/1983 | Quay | 128/303.17 |

Primary Examiner—Kyle L. Howell
Assistant Examiner—Max F. Hindenburg
Attorney, Agent, or Firm—Toren, McGeady and Goldberg

[57] ABSTRACT

A surgical combination instrument for atraumatically grasping human or animal tissue, for performing bipolar coagulation by means of high frequency current, for cutting tissue in the coagulated area and for removing tissue remaining uncoagulated between the coagulated areas. These functions can be performed without requiring a change in instruments. The cut tissue removed by means of the instrument can be made available for a histological identification.

6 Claims, 3 Drawing Figures

COMBINATION INSTRUMENT FOR LAPAROSCOPICAL TUBE STERILIZATION

BACKGROUND OF THE INVENTION

1. Field of the Invention

The invention relates to surgical instruments and, more particularly, to a combination instrument for atraumatic grasping, bipolar coagulation by means of high frequency current and cutting out human or animal tissue. The instrument is particularly intended for the purpose of making the fallopian tubes in a woman impassable by means of an abdominal specular operation, hereinbelow called laparoscopical tube sterilization.

2. Description of the Prior Art

Surgical operations have long been performed in human medicine for the purpose of sterilization, for instance, to make impassable the fallopian tubes in women or the sperm ducts in men. First used for this purpose were surgical methods in open surgery which made the organs impassable by blocking them by means of a thread and subsequently sharply cutting them.

As early as 1937, Anderson (USA) utilized the tissue destroying effect of high frequency current for laparoscopical tube sterilization in gynecology. This technique was further developed after appropriate instruments were designed, for instance, by SEMM (Germany), the companies Karl Storz GmbH and Richard Wolf GmbH. The technique is still used today for laparoscopical tube sterilization.

Two methods of coagulating tissue by means of high frequency current are used today. They are (1) the unipolar high frequency method and (2) the bipolar high frequency method.

In the unipolar high frequency method, a neutral electrode, usually attached to the thigh of the patient, forms one pole. A functional device at the laparoscopical instrument forms the other pole for the high frequency current (for instance, unipolar hooked scissors according to SEMM).

In the bipolar high frequency method, wherein both electrodes are opposite one another in the area of the functional unit of the surgical instrument (for instance, bipolar grasping forceps, Karl Storz GmbH), the high frequency current is conducted only through the tissue grasped by the functional units.

In order to perform a laparoscopical tube sterilization by coagulation with high frequency current and to remove tissue, it is presently necessary, after applying a pneumoperitoneum and inserting an optical instrument, first to grasp the tube, for instance, with the bipolar grasping forceps (Richard Wolf GmbH) and to coagulate the tube, then to remove this instrument, insert a cutting instrument, for instance, the unipolar hook-type cutter according to Frangenheim, to cut out a portion of the tube in the coagulated area, and, after another instrument change, to remove the cut tube portion from the abdominal cavity by means of grasping forceps.

The use of unipolar high frequency current for tube coagulation should be considered obsolete today because the current may cause uncontrolled burning at completely different portions of tissue which were not even touched by the surgeon.

When using the bipolar high frequency method for the coagulation of tubes, the instruments available today make it necessary, after insertion of a bipolar grasping forceps and subsequent coagulation of a tube portion, to again remove the forceps, insert a cutting device, and to cut the tube in the area which previously was coagulated. If, in addition, a tube section is to be removed, several cuts must be made which is particularly difficult with cuts at an angle of 90° to the guide sleeve of the cutting instrument, because the cutting device is rigid relative to the guide sleeve. This has the serious disadvantage that these manipulations result in cuts in non-coagulated areas and cause dangerous bleeding. In addition, the instrument must be changed for a third time in order to remove the cut out tissue from the abdominal cavity.

Since the bipolar grasping forceps used today have an electrode width of only 5 to 6 mm, the tube is grasped and coagulated several times, so that sometimes the tube is unnecessarily destroyed over its entire length.

In addition, coagulation frequently takes place far beyond the tubes in the appendages because these instruments have no stops against the electrodes and, consequently, the tissue, in this case the tubes, may reach much too deeply between the grasping units of the bipolar forceps. If tissue is successfully removed in spite of these difficulties, the removed tissue is completely destroyed by the coagulation and can be histologically identified only with difficulty or not at all. Although tissue removal for histological identification is internationally demanded, it is usually not performed because (1) the surgical risk is substantially increased, and (2) a proper histological identification is doubtful.

SUMMARY OF THE INVENTION

I have discovered a combination instrument for laparoscopical tube sterilization which overcomes the above disadvantages of conventional instruments and specifically meets the following requirements:

1. Atraumatic grasping of tissue without shifting of functional units of the instrument relative to the guide sleeve of the instrument.
2. Safe coagulation of the grasped tissue area by means of bipolar high frequency current, wherein the engagement of the functional units with one another takes place in such a way that undesirable carbonizations cannot occur. The grasped tissue is coagulated at two points, leaving an essentially non-coagulated tissue portion between the two points.
3. Cutting the tissue within the coagulated area, i.e., the bloodless tissue, using the same instrument, i.e, without changing instruments.
4. Catching and holding the essentially non-coagulated tissue portion with the same instrument and removing the tissue portion without effort from the instrument, after the instrument has been removed from the abdominal cavity, so that the tissue portion can be made available for histological examination.
5. Performing individually and independently from one another, with one instrument the work steps of atraumatic grasping, bipolar coagulation and removal of a tissue portion.

The combination instrument can also be used for detaching adhesions, removing tissue specimens and, finally, for atraumatic grasping and moving of tissue to gain an overview in diagnostic abdominal specular examinations. In addition, the combination instrument can also be used in open surgery.

This task is accomplished by a combination instrument which combines all the functions of atraumatic grasping, bipolar coagulation of tissue at two points by means of high frequency current, cutting tissue within the coagulated area, i.e., bloodless tissue, and catching the cut-out tissue portion, which is essentially non-coagulated. In addition, it is possible to also perform the described work steps independently from one another.

Since the combination instrument according to the present invention is simple and safe to handle, the time required is reduced and the surgical risk is minimized. For the first time, it is possible to perform a complete laparoscopical tube sterilization, i.e., grasping, coagulating and cutting of both tubes successively with additional tissue removal, without having to change instruments. It should be particularly emphasized that the cutting out of tissue with the new combination instrument takes place only within the coagulated area and, consequently, the risk of bleeding is significantly reduced.

In addition, a safe histological identification of the removed tissue portion is now possible because the tissue portion removed with the combination instrument is essentially non-coagulated. The safe histological identification of the removed tissue is particularly important when operating on the tuba uterina. The tuba uterina is located in the close vicinity of the ligamentum rotundum and it is necessary to identify the tissue which has been cut out in order to ensure that it is indeed the tuba uterina which has been operated on and has been made impassable.

The combination instrument according to the present invention has the advantage that a later refertilization is possible because the tuba uterina is coagulated and interrupted at only one location along a length which corresponds to the width of the instrument. As a result, the tuba uterina is not destroyed along its entire length as is common at the present time.

The cutting device of the combination instrument serves as a stop for the tube portion to be coagulated, so that an unintended coagulation deep into the tube appendages is prevented. The grasping elements of the combination instrument move toward one another during closing, so that the tissue grasped at the points to be coagulated, is uniformly pressed together and, consequently, an optimum atraumatic grasping and/or coagulation is possible. Also, during use, the grasping and cutting elements of the instrument do not move relative to the guide sleeve, so that a safe grasping of the tissue is possible. Due to this construction of the combination instrument, tissue other than tubes, for instance, adhesion strands can be grasped, coagulated bipolarly and cut bloodlessly. Depending on its width, the tissue strand can be grasped and coagulated once again and then cut further so that a path is cut through the tissue wherein the cut edges coagulate all around, i.e., are bloodless.

The combination instrument according to the invention can be used for (1) laparascopy, (2) laparotomy, and (3) posterior colpotomy.

The principal use is in the field of laparoscopical tube sterilization. But the instrument can also be used for the detachment of adhesions, the removal of tissue samples and the lifting of tissue, i.e, atraumatic grasping and moving of tissue, to gain an overview in diagnostic laparoscopies.

The combination instrument is simple to clean without having to be disassembled, and it is maintenance free. It can be sterilized with all conventional sterilization methods.

DESCRIPTION OF THE PREFERRED EMBODIMENT

Figure 1:
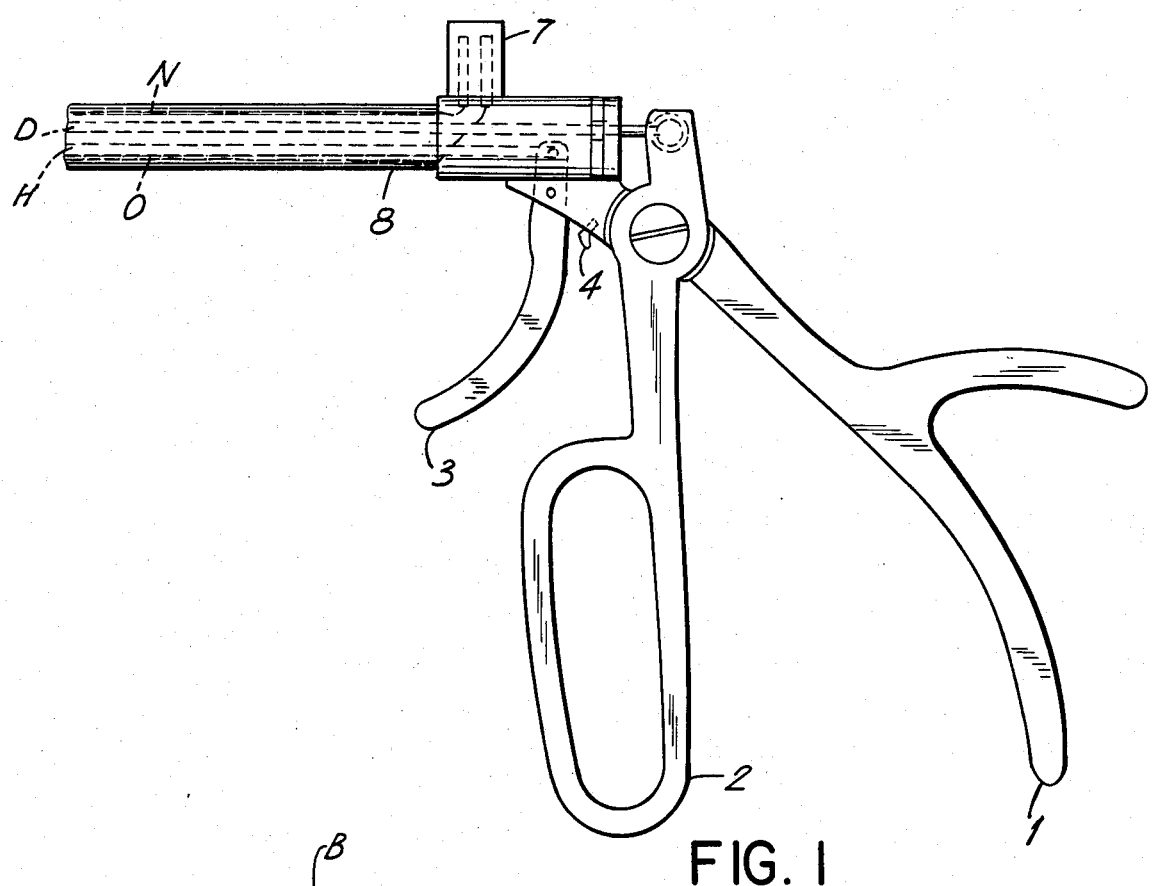
FIG. 1 is a partial elevational view of a combination instrument according to the present invention, wherein the functional unit is broken away.
Figure 2:
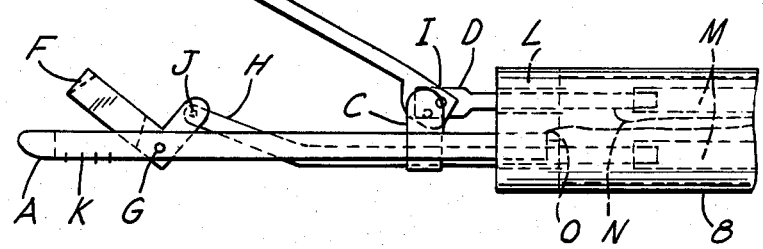
FIG. 2 is an elevational view of the functional unit of the instrument.
Figure 3:
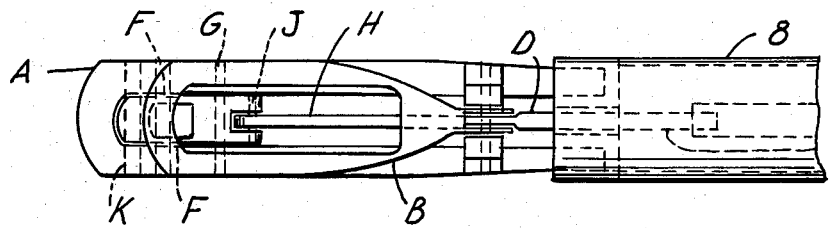
FIG. 3 is a plan view of the functional unit.

The combination instrument shown in FIG. 1 includes a grip member which is held in the hand. The functional unit illustrated in FIGS. 2 and 3 is constructed in such a way that its individual parts can be moved toward one another. These movements are transmitted by means of rods onto a grasping device A and B and a cutting device F.

The grip member has three grip elements. Grip elements 2 and 3 are attached at grip element 1 and are pivotable relative to this element.

A guide sleeve 8 is attached at grip element 1. Guide sleeve 8 houses push and pull rods D and H which are moved by means of grip elements 2 and 3, respectively.

Adjacent the grip member, guide sleeve 8 has mounted on it a plug device 7 which is insulated from the guide sleeve and is used for the high frequency current supply. In addition, in the guide sleeve there are the conductors N and O which connect the plug device 7 with the grasping devices A and B. The guide sleeve 8 is lined on the inside with an insulating layer.

Arranged at the end of the guide sleeve opposite the grip member, there is the functional unit which is capable of performing three functions: grasping, coagulating and cutting.

The functional unit includes the grasping devices A and B and the cutting device F. The stationary grasping device A serves as abutment for the pivotable grasping device B. For this purpose, the joint C is provided on grasping device A. Grasping devices A and B serve as the electrodes for high frequency current. The grasping device A is insulated from B in joint C. The push and pull rod D is attached at joint C to grasping device B. Thus, using rod D, the grasping device B can be opened to approximately 60° in relation to the grasping device A which makes a secure grasping of the tissue possible.

Inside the grasping device A which, for this purpose, is U-shaped, there is a cutting device F which is pivotable in the grasping device about a joint G. The push and pull rod H is connected to cutting device F by means of a joint J. Opening of the cutting device F in relation to the grasping device A is also possible to approximately 60°. In the closed position, the cutting device F is lowered into grasping device A.

The grasping device B and the stationary grasping device A are arranged in such a way that they approach one another uniformly along the entire length of the grasping distance of the tissue. In other words, the tissue is pressed by the movable grasping device B uniformly onto the stationary grasping device A, so that all grasped tissue portions can be coagulated uniformly.

The grasping device A has an opening for the cutting device F. A wire basket K to catch the cut out tissue portions is provided underneath this opening. The cutting device F is constructed in such a way that, during cutting, the resected tissue is pressed into the wire basked K. The wire basket K can hold several tissue pieces, so that a complete sterilization can be performed without changing instruments, i.e., two tubes can be operated on successively.

The grasping device A is connected rigidly with the guide sleeve 8 by means of an insulating element L. The insulating element L also serves to guide the push and pull rods D and H. Inside the guide sleeve 8, a portion each of rods D and H are formed by insulating elements M.

The grasping device B is pivoted by means of gripping member 2 and push and pull rod D. The cutting device F is moved by means of gripping element 3 and push and pull rod H. The lever path of the gripping element 3 is set by means of the setting screw 4.

A laparoscopical tube sterilization is performed with the combination instrument according to the present invention as follows:

After the application of a pneumoperitoneum and insertion of an optical instrument, the combination instrument is inserted into the abdominal cavity by means of a second paracentesis with a conventional 10 mm trocar (manufactured, e.g., by Wolf GmbH). The plug device 7 of the instrument is connected to a conventional bipolar high frequency current generator.

After locating a tube and opening the grasping device B and the cutting device F, the tube is grasped by closing the grasping device B and pressing it against the stationary grasping device A. Now the high frequency current is conducted through grasping devices A and B, so that the tube is coagulated in a U-shape between the grasping devices A and B. After completion of the coagulation step, without opening the grasping device B, the cutting device F is actuated and the tube portion located within the coagulated area is cut out and pressed into the wire basket K. Then, the grasping device B is opened. This completes the steps of rendering the tube impassable and the removal of tissue. For a complete sterilization, the same steps are performed at the second tube without changing instruments. When the instrument is removed from the abdominal cavity, the tissue portions lying on top of one another in the operating sequence are removed and a histological examination is performed. This is particularly necessary for forensic reasons.

I claim:

1. A surgical combination instrument, comprising means for grasping human or animal tissue, the grasping means including first and second grasping members, the second grasping member connected and pivotally movable relative to the first grasping member between an open and a closed position of the grasping means, the grasping members defining central openings aligned with one another when the grasping means is in the closed position, the first and second grasping members electrically insulated from one another and forming electrodes for high frequency current to be utilized for bipolar coagulation of the tissue grasped by the grasping means, cutting means attached and pivotable relative to the grasping members in the central opening thereof for cutting the non-coagulated portion of tissue extending across the aligned openings of the grasping means, wherein the cutting means (F) is U-shaped in its transverse direction and is pivotally hinged inside the opening (E) of the stationary first grasping member (A) about a joint (G) and lowered in the closed position of the cutting device (F) into the opening (E) of the stationary first grasping member (A) and to be entirely receivable within the central opening (E) of the stationary first grasping member (A), and wherein underneath the opening (E) of the stationary first grasping member (A) is provided in a holding means (K) forming part of the stationary first grasping member (A) for catching the tissue portion cut by the cutting device (F) and forced into the holding means (K) by the cutting device (F).

2. The surgical instrument according to claim 1, wherein said holding means is a wire basket extending across said central opening of said first grasping member.

3. The surgical instrument according to claim 1, wherein said grasping means and said cutting means can be operated independently from one another.

4. The surgical instrument according to claim 1, wherein said grasping members extend parallel to one another when said grasping means is in said closed position.

5. The surgical instrument according to claim 1, wherein the grasping members (A) and (B) are atraumatical grasping means.

6. A method for removing tissue from a human or animal body with a surgical combination instrument having grasping, coagulation and holding means comprising a pivotable member (B) and a stationary member (A), and having a cutting device (F), comprising the steps of locating the tissue, opening together the pivotable member (B) and the cutting device (F), locating tissue between cutting device (F) and stationary member (A), abutting the opened cutting device (F) against the tissue, grasping the tissue by closing the pivotable member (B) and pressing it against stationary member (A), coagulating an area of the tissue with coagulating means, members (A) and (B) supplied with high frequency current, and cutting through the tissue portion located within the coagulated area with cutting device (E) and pressing the tissue into the holding means with cutting device (F).

* * * * *